United States Patent [19]
Domb et al.

[11] Patent Number: 5,179,189
[45] Date of Patent: Jan. 12, 1993

[54] FATTY ACID TERMINATED POLYANHYDRIDES

[75] Inventors: Abraham J. Domb; Manoj Maniar, both of Baltimore, Md.

[73] Assignee: Nova Pharmaceutical Corporation, Baltimore, Md.

[21] Appl. No.: 756,483

[22] Filed: Sep. 9, 1991

Related U.S. Application Data

[63] Continuation-in-part of Ser. No. 467,635, Jan. 19, 1990.

[51] Int. Cl.$^5$ ............................................. C08G 67/04
[52] U.S. Cl. ................................. 528/271; 528/206; 528/327; 528/321; 528/360; 528/361
[58] Field of Search .................... 526/318.2; 528/271, 528/206, 327, 321, 360, 361

[56] References Cited

U.S. PATENT DOCUMENTS

| | | | |
|---|---|---|---|
| 4,501,877 | 2/1985 | Fagerburg | 528/271 |
| 4,526,957 | 7/1985 | Matz | 528/271 |
| 4,757,128 | 7/1988 | Domb et al. | 528/271 |
| 4,789,724 | 12/1988 | Domb et al. | 528/176 |
| 4,792,598 | 12/1988 | Ziegast | 528/271 |
| 4,857,311 | 8/1989 | Domb et al. | 424/78 |
| 4,868,265 | 9/1989 | Gupta | 528/271 |
| 4,868,274 | 9/1989 | Gupta et al. | 528/271 |
| 4,886,870 | 12/1989 | D'Amore et al. | 528/206 |
| 4,888,176 | 12/1989 | Langer et al. | 424/426 |
| 4,891,225 | 1/1990 | Langer et al. | 424/428 |
| 4,916,204 | 4/1990 | Domb et al. | 528/271 |
| 4,933,431 | 6/1990 | Domb et al. | 528/271 |

FOREIGN PATENT DOCUMENTS 684685 4/1964 Canada ........................... 528/271

OTHER PUBLICATIONS

"Bioerodible Polyanhydrides for controlled drug delivery" Rosen et al–Biomaterials 1983 vol. 4 April.
"Bioerodible polyanhydride as drug carrier matrices I" Leong et al.–Journal of Biomedical Materials Res. vol. 19, 941–955 (1985).
"Bioerodible polyanhydrides as drug carrier matrices II" Jour. of Biomedical Materials Res. vol. 20, 51–64 (1986).

*Primary Examiner*—Joseph L. Schofer
*Assistant Examiner*—N. Sarofim
*Attorney, Agent, or Firm*—Kilpatrick & Cody

[57] ABSTRACT

Fatty acid terminated polyanhydrides suitable for use as controlled release matrices in biodegradable sustained release drug delivery systems and methods for making thereof are described. The polymers are more soluble in organic solvents, and have a lower melting point than the corresponding non-fatty acid terminated polyanhydrides. The fatty acid terminated polyanhydrides are also more hydrophobic than the corresponding polyanhydrides that are not terminated with a fatty acid, and combine the properties of thermodynamic and hydrolytic stability, and easy storage. The polymers can be produced with a controlled and low molecular weight. The polyanhydrides are useful in a number of applications, including as a matrix in biodegradable drug delivery systems.

13 Claims, 2 Drawing Sheets

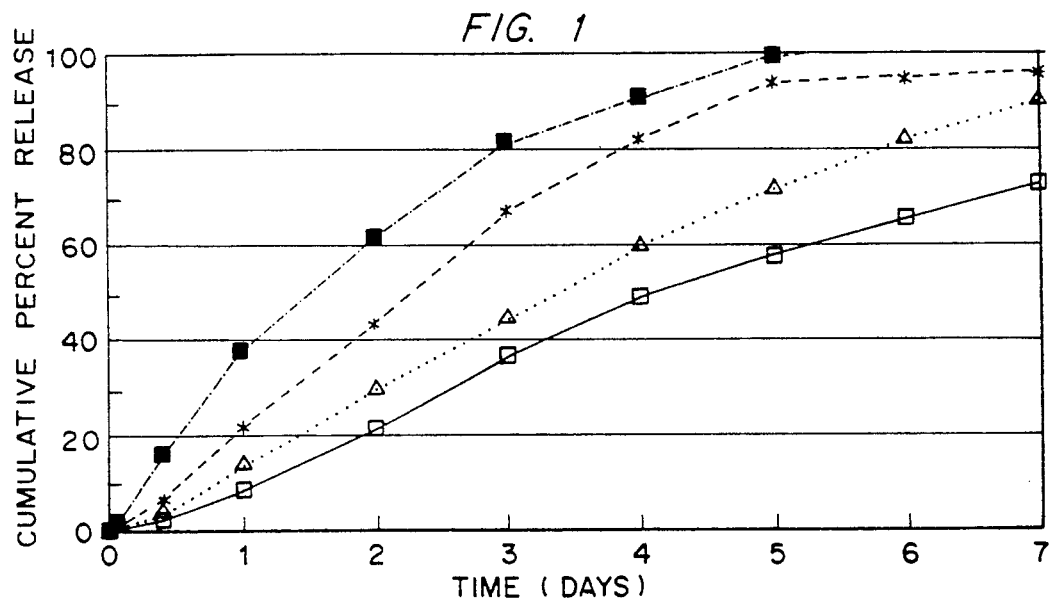
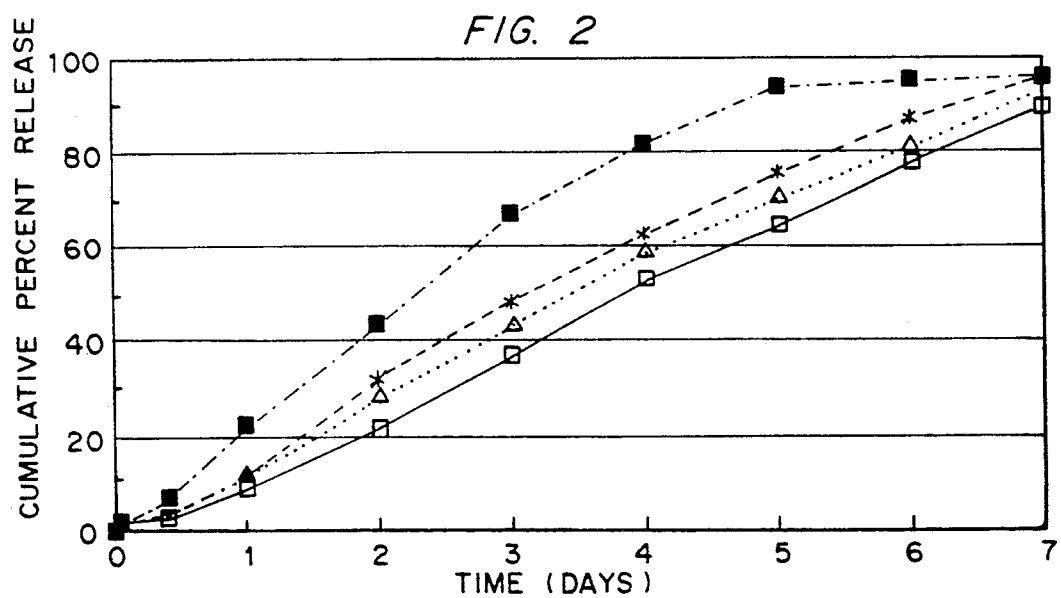

FATTY ACID TERMINATED POLYANHYDRIDES

This application is a continuation-in-part of U.S. Ser. No. 07/467,635, which is now pending, entitled "Polyanhydrides of Oligomerized Unsaturated Aliphatic Acids" filed on Jan. 19, 1990, by Abraham J. Domb.

BACKGROUND OF THE INVENTION

This invention is in the area of polymers for controlled delivery of substances, and more specifically encompasses biodegradable polyanhydrides whose end groups are terminated with fatty acids, and methods for making thereof.

There has been extensive research in the area of biodegradable controlled release systems for bioactive compounds. Biodegradable matrices for drug delivery are useful because they obviate the need to remove non-biodegradable drug-depleted devices. The ideal polymeric matrix would combine the characteristics of hydrophobicity, stability, organic solubility, low melting point, and suitable degradation profile. Such a polymer must be hydrophobic so that it retains its integrity for a suitable period of time when placed in an aqueous environment, such as the body, and stable enough to be stored for an extended period before use. The ideal polymer must also be strong, yet flexible enough so that it does not crumble or fragment during use.

Controlled release devices are typically prepared in one of several ways. For example, the polymer can be melted, mixed with the substance to be delivered, and then solidified by cooling. Such melt fabrication processes require polymers having a melting point that is below the temperature at which the substance to be delivered and polymer degrade or become reactive. Alternatively, the device can be prepared by solvent casting, where the polymer is dissolved in a solvent, and the substance to be delivered dissolved or dispersed in the polymer solution. The solvent is then evaporated, leaving the substance in the polymeric matrix. Solvent casting requires that the polymer be soluble in organic solvents.

Many polymers have been evaluated for their suitability for use as a matrix for a delivery device, including polyesters, polyamides, polyurethanes, polyorthoesters, polyacrylonitriles, and polyphosphazenes. None of these polymers have exhibited all of the desired characteristics for use in the controlled delivery of substances.

Polyanhydrides have also been studied for use in controlled delivery devices, as reported by Leong, et al., *J. Med. Biomed. Mater. Res.* 19, 941 (1985); and *J. Med. Biomed. Mater. Res.* 20, 51 (1986). One of the first polyanhydrides studied for its controlled release behavior was poly(bis(p-carboxyphenoxy)methane anhydride), described by Rosen, et al., *Biomaterials* 4, 131 (1983). The aromatic polyanhydride exhibited near zero order (linear) erosion and release kinetics at 37° C. and 60° C. Shortly thereafter, three related polyanhydrides: poly 1,3-(bis(p-carbophenoxy)propane anhydride (p-CPP) (an aromatic polyanhydride); the polymer formed from the copolymerization of p-CPP with sebacic acid (a copolymer of an aromatic diacid and an aliphatic diacid); and polyterephthalic acid (an aromatic anhydride), were prepared and examined for release rates by Leong, et al., *J. Med. Biomed. Mater. Res.* 19, 941 (1985).

These aromatic polyanhydrides were found to have unacceptably slow degradation rates. For example, it was estimated that it would take a delivery device prepared from p-CPP more than three years to completely degrade in vivo. Further, anhydride homopolymers based on aromatic or linear aliphatic dicarboxylic acids were found to be highly crystalline and have poor film forming properties. Aromatic polyanhydrides also have high melting points and low solubility in organic solvents.

Polymers prepared from linear aliphatic diacids are hydrophilic solids that degrade by bulk erosion, resulting in a rapid release of the drug from the polymeric matrix. Consequently, linear aliphatic diacids are unsuitable for use in controlled drug delivery systems. Hydrophobicity of such polymers can be increased by copolymerizing the linear aliphatic diacids with aromatic diacids. This approach, however, results in an increase in the polymer melting temperature and a decrease in solubility in organic solvents. Furthermore, such copolymerization does not improve the drug release profile, but instead increases the degradation and the elimination time of the polymer both in vivo and in vitro. Since both homopolymers and copolymers of linear aliphatic diacids are very sensitive to moisture, they require storage under anhydrous and low temperature conditions.

As described in U.S. Pat. No. 4,757,128 to Domb and Langer, high molecular weight copolymers of aliphatic dicarboxylic acids with aromatic diacids are less crystalline than aromatic or linear aliphatic polyanhydrides, and they form flexible films. Degradation rates are also increased by copolymerizing an aromatic dicarboxylic acid with an aliphatic diacid. However, bulk erosion still occurs because areas of the polymer containing aliphatic anhydride linkages erode faster than aromatic anhydride linkages, forming channels in the matrix through which the substance to be delivered is released in an uncontrolled fashion. For example, in the p-CPP sebacic acid copolymer described above, the aliphatic anhydride bonds are cleaved in vivo and all of the drug is released in ten days, while the aromatic regions remain intact for another five and one-half months. Further, the copolymers have inferior mechanical properties; they become brittle and crumble into flakes on exposure to moisture.

U.S. Patents that describe the use of polyanhydrides for controlled delivery of substances include: U.S. Pat. No. 4,857,311 to Domb and Langer, entitled "Polyanhydrides with Improved Hydrolytic Degradation Properties," which describes polyanhydrides having a uniform distribution of aliphatic and aromatic residues in the chain, prepared by polymerizing a dicarboxylic acid with an aromatic end and an aliphatic end; U.S. Pat. No. 4,888,176 to Langer, et al., entitled "Controlled Drug Delivery High Molecular Weight Polyanhydrides," which describes the preparation of high molecular weight polyanhydrides in combination with bioactive compounds for use in controlled delivery devices; and U.S. Pat. No. 4,789,724 to Domb and Langer, entitled "Preparation of Anhydride Copolymers", which describes the preparation of very pure anhydride copolymers of aromatic and aliphatic diacids.

There remains a strong need, however, for a polymer having the desired characteristics of hydrophobicity, stability, strength, flexibility, organic solubility, low melting point, and appropriate degradation profile, for use as a matrix for controlled delivery devices. It would also be useful to be able to substantially alter the degradation and release kinetics of the polyanhydride for a wide variety of applications without significantly affecting the physical properties of the polymer.

It is therefore an object of the present invention to provide a biodegradable polymer that releases an incorporated substance in a controlled manner, wherein the polymer is highly hydrophobic, and degrades by surface erosion.

It is a further object of the present invention to provide a biodegradable, surface erodible polymer that is thermodynamically and hydrolytically stable, and can be stored under mild storage conditions.

It is a still further object of the present invention to provide a biodegradable controlled release microparticulate, injectable delivery system suitable for controlled in vivo administration of peptides and proteins, which is not acidic even in the absence of additives, and which stabilizes the incorporated peptides and proteins to be released without the use of additives.

SUMMARY OF THE INVENTION

Fatty acid terminated polyanhydrides, and their method of preparation, are disclosed. While not limited, in a preferred embodiment, the fatty acid terminated polyanhydrides have the general structure:

$$R'-\overset{O}{\underset{\|}{C}}-O+\overset{O}{\underset{\|}{C}}-R-\overset{O}{\underset{\|}{C}}-O\underset{\overline{n}}{+}\overset{O}{\underset{\|}{C}}-R'$$

wherein R is an aliphatic, aromatic, or heterocyclic moiety, R' is a linear fatty acid residue of $C_6$ to $C_{22}$, and n is an integer from to 1 to 500. The polymers are highly hydrophobic, thermodynamically and hydrolytically stable, easily storable, and can be produced with a controlled and low molecular weight. The fatty acid terminated polyanhydrides are more soluble in organic solvents, and have a lower melting point, than the corresponding polyanhydrides that are not terminated with fatty acid moieties.

The fatty acid terminated polyanhydrides are particularly useful in biodegradable drug delivery systems since they do not create an acidic microenvironment when degrading, and they stabilize, without additives, proteins and peptides to be released from such systems.

BRIEF DESCRIPTION OF THE DRAWINGS

FIG. 1 is a graph comparing the percent release of marcaine free base (FB) from fatty acid terminated polyanhydride as a function of time (days): p(STA-SA)(15:85) with 10% marcaine FB (open square); p(STA-SA)(10:90) with 10% marcaine FB (open triangle); p(STA-SA)(5:95) with 10% marcaine FB (-*-); and p(SA) with 10% marcaine FB (closed square).

FIG. 2 is a graph comparing the percent release of marcaine HCl from fatty acid terminated polyanhydride as a function of time (days): p(STA-SA)(15:85) with 10% marcaine FB (open square); p(STA-SA)(10:90) with 10% marcaine FB (open triangle); p(STA-SA) (5:95) with 10% marcaine FB (-*-); and p(SA) with 10% marcaine FB (closed square).

DETAILED DESCRIPTION OF THE INVENTION

Figure 3:
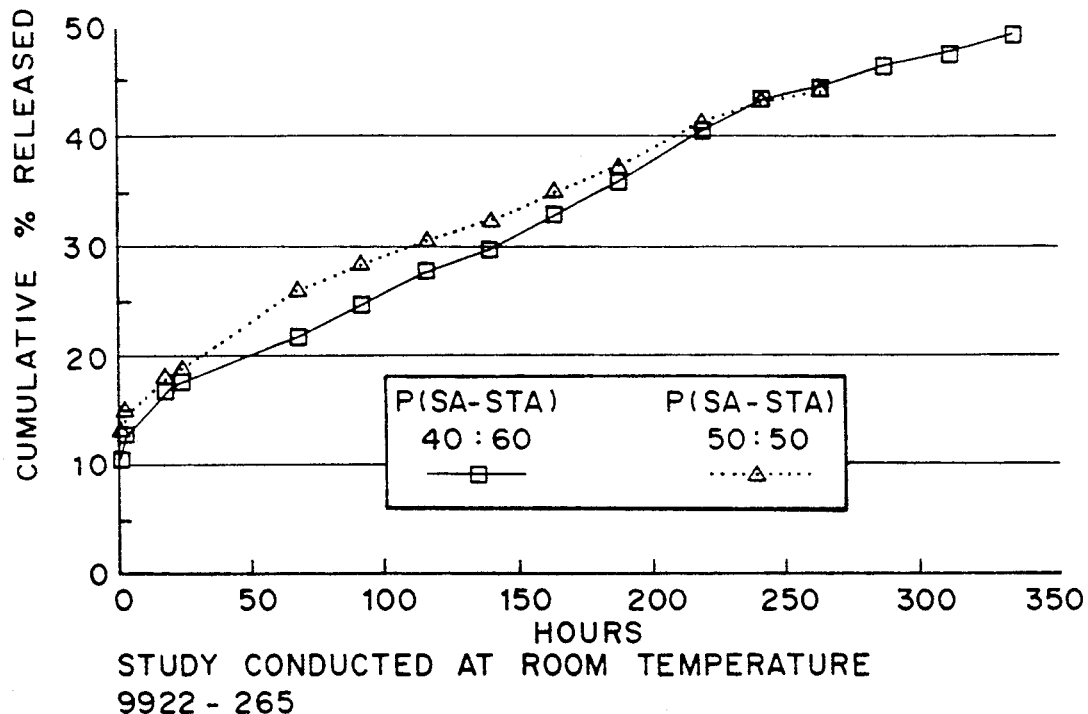
FIG. 3 is a graph comparing the cumulative percent release of BSA from fatty acid terminated polyanhydride particles as a function of time (hours) for p(STA-SA)(40:60) (open square) and p(STA-SA)(50:50) (open triangle).

As used herein, the term aliphatic refers to a linear, branched, or cyclic alkane, alkene, or alkyne. Preferred aliphatic groups in the disclosed polyanhydride are $C_4$ to $C_{22}$ linear, or branched moieties, particularly $C_4$ to $C_{22}$ linear alkyl moieties.

As used herein, the term aromatic refers to an unsaturated cyclic carbon compound with $4n+2$ $\pi$ electrons.

As used herein, the term heteroaromatic refers to an aromatic compound that has an atom other than carbon in the ring, for example, nitrogen, oxygen or sulfur.

As used herein the term fatty acid refers to a long chain ($C_6$ to $C_{22}$) aliphatic carboxylic acid.

As used herein the abbreviations STA and SA refer to stearic acid and sebacic acid, respectively.

The biodegradable compositions disclosed herein are polyanhydride polymers which, during the polymerization process, are terminated with fatty acid molecules. Natural fatty acids act as polymer chain terminators because they only have one carboxylic acid group. They are, therefore, useful in controlling and limiting the molecular weight of the polyanhydride polymer. Such polymers may be either high molecular weight or low molecular weight. The low and controlled molecular weight fatty acid terminated polyanhydrides require less stringent storage conditions, due to reduced depolymerization relative to that observed with higher molecular weight polyanhydrides described by A. Domb and R. Langer, *Macromolecules*, 22, 2117 (1989). Such polymers perform equally well or better than currently known polyanhydrides as carriers for the controlled release of substances.

The incorporation of long chain fatty acids such as stearic acid into polyanhydride polymers alters the hydrophobicity of the polymer and decreases their degradation rate.

Fatty acid terminated polyanhydrides can be prepared in several ways. In a preferred embodiment, decarboxylic acids and the fatty acids are reacted separately with a lower ($C_1$ to $C_5$) aliphatic anhydride or acid chloride to form mixed anhydrides, referred to below as "prepolymers," as described in U.S. Pat. No. 4,757,128, incorporated by reference herein. These prepolymers are then mixed and co-polymerized. Once synthesized, the polymers can be combined with various substances or drugs sought to be released in a controlled manner and the mixture formed into biodegradable devices by methods well known to those skilled in the art.

Dicarboxylic Acid Monomers

Monomers useful in the preparation of the dicarboxylic acid prepolymers are those of the structure $HO_2C-R-CO_2H$, wherein R is an aliphatic, aromatic, or heterocyclic moiety. Nonlimiting examples are aliphatic dicarboxylic acids, as defined by the formula: $HOOC-H_2C-Y-CH_2-COOH$; aromatic dicarboxylic acids, as defined by the formulas:

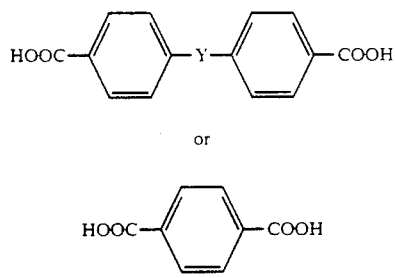

aromatic-aliphatic dicarboxylic acid, as defined by the formula:

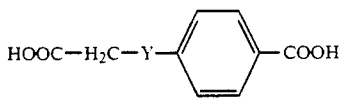

aliphatic heterocyclic dicarboxylic acids defined by the formula:

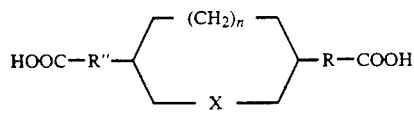

wherein $X=0$, N or S, $n=1$ to 3; aromatic heterocyclic dicarboxylic acids, and aromatic heterocyclic aliphatic dicarboxylic acids.

The formulas are to be construed to include substitutions on the aromatic or aliphatic groups of the dicarboxylic acid. The Y group is any divalent organic radical, for example an aliphatic aromatic, or heteroaromatic moiety, and $R=R''$. Any combination of these dicarboxylic acids can be copolymerized. For example, aromatic and aliphatic heterocyclic dicarboxylic acids can be used in combination with aliphatic dicarboxylic acids. Aromatic diacids can be used in combination with aliphatic acids. Further, combinations of aromatic, aliphatic and aromatic-aliphatic dicarboxylic acids can be polymerized.

The following monomers are examples of suitable dicarboxylic acids: sebacic acid, phthalic acid, terephthalic acid, isophthalic acid, adipic acid, 1,10-dodecanoic acid, bis(p-carboxyphenoxyalkane), fumaric acid, 1,4-diphenylenediacrylic acid, branched monomers such as 1,3,5-benzenetricarboxylic acid, azeleic acid, pimelic acid, suberic acid (octanedioic acid), itaconic acid, biphenyl-4,4'-dicarboxylic acid, and benzophenone-4,4'-dicarboxylic acid, p-carboxyphenoxyalkanoic acid, hydroquinone-0,0-diacetic acid, 1,4-bis-carboxymethyl benzene, 2,2-bis-(4-hydroxyphenyl)propane-0,0-diacetic acid, 1,4-phenylene-dipropionic acid, and cyclohexane dicarboxylic acid.

Monomers should be chosen that produce a fatty acid terminated polyanhydride with the desired properties. For example, aliphatic dicarboxylic acids of $C_4$ to $C_{22}$ can be used to increase hydrophobicity and moldability of the polymer. Aromatic dicarboxylic acids can be used to increase the solubility of the polyanhydride in common organic solvents and to decrease the melting point of the polyanhydride.

Fatty Acid Chain Terminators

Natural fatty acids that can be used to alter the properties of the polyanhydride polymers and control their molecular weights include, but are not limited to, caproic, caprylic, capric, lauric, myristic, palmitic, stearic, arachidic, behenic, lignoceric, heptanoic, nonanoic, undecanoic, tridecanoic, pentadecanoic, heptadecanoic, nonadecanoic, heneicosanoic, and tricosanoic acids. Naturally occurring unsaturated fatty acids, including arachidonic, docosahexanoic, elaidic, erucic, linoleic, linolenic, nervonic, oleic, palmitoleic and petriselinic acids can also be used to prepare the fatty acid terminated polyanhydrides.

The physical properties of the polyanhydride can be manipulated by careful selection of the fatty acid used to terminate the polymer. Short chain fatty acids ($C_6$ to $C_{12}$) can be used to decrease the molecular weight of the polyanhydride with minimal effect on the hydrophobicity characteristics of the polymer. Unsaturated fatty acids, such as erucic and oleic acid, which have a lower melting point than the corresponding saturated fatty acid, are useful to decrease the melting point of the polyanhydride. Long chain fatty acids ($C_{12}$ to $C_{22}$), can be used to increase the hydrophobicity of the polyanhydride.

Methods for Polymerizing Fatty Acid Terminated Polyanhydrides

Any ratio of fatty acid units to dicarboxylic acid units can be used that produces a polyanhydride with the desired properties. A preferred ratio of fatty acid units to dicarboxylic acid units in the polyanhydride is 2 to 1000 fatty acid units per 500 units of dicarboxylic acid monomers. A ratio of approximately 85% by weight of dicarboxylic acid to 15% by weight of fatty acid is preferred in the preparation of certain fatty acid terminated polyanhydrides, including those made from sebacic acid and stearic acid.

Fatty acid terminated polyanhydrides can be prepared by methods known to those skilled in the art, including melt polycondensation and solution polymerization of the selected dicarboxylic acid with the desired amount of fatty acid.

Using the method of melt polycondensation, described by Domb, et al., in *J. Poly. Sci* 25, 3373 (1987), prepolymers can be prepared by heating the diacid and fatty acid separately with a lower aliphatic anhydride or lower aliphatic acid chloride to form the corresponding dialiphatic dianhydride ("diacid prepolymer") and aliphatic fatty acid anhydride ("fatty acid prepolymer"). These prepolymers are then mixed in the desired ratio and heated neat under vacuum to form the fatty acid terminated anhydride polymer. In a preferred embodiment, acetic anhydride is used to prepare the prepolymer. The aliphatic acid is stripped off during the polymerization process. Combinations of dialiphatic dianhydrides and combinations of fatty acid prepolymers can also be polymerized with this method.

In a preferred embodiment, the fatty acid and dicarboxylic acid prepolymers are heated at 150° C. to 220° C. in a vacuum of greater than 1 mm Hg, for a time ranging from 30 minutes to six hours. The polymerization time depends on the batch size, and on the monomer composition.

Solution polymerization is preferred when either the fatty acid or the dicarboxylic acid is sensitive to heat. Solution polymerization is described in U.S. Pat. No.

4,916,204 to Domb et al., entitled "One Step Polymerization of Polyanhydrides", incorporated herein by reference. Solution polymerization involves the phosgene coupling of diacids with each other and with the fatty acid in an organic solvent. Poly(4-vinylpyridine-2% divinylbenzene) ("PVP") is added to remove the HCl from solution. For example, diphosgene (0.50 equivalents) is added dropwise to a stirred mixture of the desired ratio of dicarboxylic acid and fatty acid and poly(4-vinylpyridine-2% divinylbenzene) (in a ratio of 2 to 3 equivalents to 1 equivalent of monomer) in a suitable amount of chloroform. The solution is stirred for 3 hours at 25° C. The insoluble PVP.HCl is removed by filtration. The solvent is then removed and the precipitate is isolated, washed with ethyl ether, and then dried at 25° C. for 24 hours in a vacuum oven.

In an alternative embodiment, using either melt polycondensation or solution polymerization, the dicarboxylic acid units are allowed to polymerize alone for a given time period, and then the fatty acid terminator is added.

Materials to be Incorporated

A variety of materials, including proteins, carbohydrates, and organic molecules, can be incorporated into the polymers using known methods, including melt casting, solvent preparation, pressing, compression molding, spray drying, microencapsulation, and tableting. The polymers are particularly useful for the controlled release of proteins and peptides. Examples include drugs and other bioactive substances to be released in vivo, such as chemotherapeutic agents, antibiotics, antivirals, antifungals, antiinflammatories, and anticoagulants, as well as other substances such as fertilizers, herbicides, insecticides and repellents, that are released over a period of time. The substances to be incorporated should not chemically interact with the polymer during fabrication, or during the release process. Additives such as inorganic salts, BSA (bovine serum albumin), and inert organic compounds can be used to alter the profile of substance release.

The method of producing fatty acid terminated polyanhydrides, for ease of illustration, is described in detail below for the polymerization of sebacic acid terminated with stearic acid. The method, however, can be used to produce other polymers wherein the ratio of stearic acid to sebacic acid varies. Further, other polymers can be prepared by substituting other fatty acids for stearic acid, and other dicarboxylic acids for sebacic acid.

EXAMPLE 1

Preparation of Fatty Acid Terminated Polymers

A. Preparation of Pre-Polymers of Stearic Acid and Sebacic Acid

Stearic acid (100 g) was refluxed in acetic anhydride (500 ml) for 20 to 60 minutes. The clear solution was cooled to room air over several hours, during which time a heavy white precipitate appeared. The precipitate was collected by filtration and washed with a 1:1 hexane:diethyl ether mixture and dried. The prepolymer (>80% yield) melted at 60°-65° C. and showed typical anhydride peaks at 1740 and 1800 cm-1.

The sebacic acid prepolymer was prepared as follows. Sebacic acid (SA, 200 gm, recrystallized twice in ethanol) was added to 500 ml of hot acetic anhydride (>100° C.) and heated for 20 to 60 minutes. The clear solution was filtered through a filter paper and evaporated to dryness. To the clear residue 100 ml of dichlormethane or hot isopropylether was added and the mixture was precipitated in 1000 mL of isopropylether at room temperature. The white precipitate was collected by filtration and stored in glass containers (yield >80%). The prepolymer melted at 75°-78° C. and showed typical anhydride peaks at 1740 and 1800 cm-1. The optical density of a 2% solution in dichloromethane at 420 nm was 0.001, indicating high purity.

B. Polymerization of the Prepolymers

Figure 4:
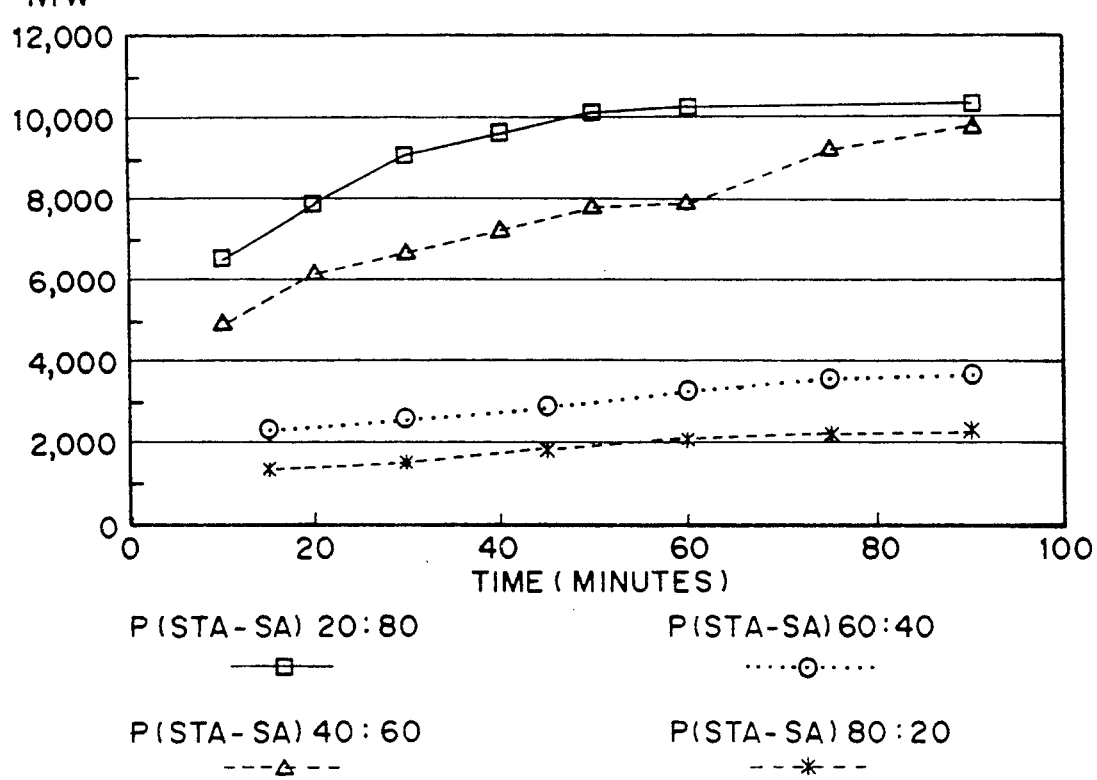
FIG. 4 is a graph of the change in molecular weight of poly (STA-SA)20:80 (open square), poly(STA-SA)40:60 (open triangle), poly(STA-SA)60:40 (open circle), and poly(STA-SA) 80:20 (*) over time in minutes.

Polymers containing varying combinations of sebacic acid prepolymers and stearic acid prepolymers were synthesized by melt polycondensation polymerization at 180° C. Samples were taken periodically as a function of time in order to monitor the molecular weight changes of the polymer. As illustrated in FIG. 4, it was found that the synthesized fatty acid terminated polyanhydride polymers ("p(STA:SA)") reached their maximum molecular weight within 90 minutes, and thereafter no significant change in molecular weight was observed. In contrast, the molecular weight of sebacic acid only polymer ("p(SA)") increased significantly after 90 minutes. Further, at any given time point in the polymerization process the molecular weight of the sebacic acid polymer p(SA) was significantly higher than that of the fatty acid terminated polymer p(STA:SA).

Representative molecular weights and intrinsic viscosity values of the fatty acid terminated polymer and P(SA) were measured as a function of time and are shown in Table I. p(STA:SA)(15:85) represents fatty acid terminated polymer prepared using 15% stearic acid prepolymer and 85% sebacic acid prepolymer by weight. As can be seen from Table I, stearic acid effectively acts as a chain terminator, so that the molecular weight of the p(STA:SA)15:85 fatty acid terminated polymers are lower than p(SA) and remain relatively constant during 90 to 150 minutes of polymerization.

TABLE I

| Comparison of Weight Average Molecular Weights and Viscosity of p(STA:SA) and p(SA). | | | | |
|---|---|---|---|---|
| Time (min) | Mw of P(STA:SA); 15:85 w/w | Mw of P(SA) | Viscosity P(STA:SA); 15:85 w/w | Viscosity P(SA) |
| 15 | 7537 | 18301 | 0.178 | 0.290 |
| 30 | 12419 | 24682 | 0.190 | 0.330 |
| 45 | 16570 | 42367 | 0.202 | 0.365 |
| 60 | 18792 | 52865 | 0.216 | 0.423 |
| 75 | 20059 | 64925 | 0.224 | 0.550 |
| 90 | 28233 | 74320 | 0.280 | 0.565 |
| 150 | 32986 | 202019 | 0.269 | 0.791 |

In the following examples, for ease of illustration, degradation and release profiles of fatty acid terminated polyanhydrides are described with reference to polymers prepared from stearic acid and sebacic acid. However, it should be understood that the present invention is not limited to these polymers but includes the use of all of the above described fatty acid terminated polyanhydrides to provide controlled release of substances.

EXAMPLE 2

Release of Marcaine Free Base and Hydrochloride Salt from P(STA:SA)

Marcaine HCl salt was powdered using pestle and mortar. The powdered drug was sieved through a 63μ sieve. Marcaine free base was purchased from Sigma Chemical Company, with a particle size of less than 30 microns. P(STA:SA)(15:85) prepolymers and p(SA) prepolymers were prepared as described in Example 1. Other fatty acid terminated polyanhydrides composed of 10% stearic acid:90% sebacic acid and 5% stearic acid:95% sebacic acid were prepared by the method described in Example 1, except that the initial concentrations of stearic acid and sebacic acid were as indicated. The resulting fatty acid terminated polymers and were designated p(STA:SA)(10:90) and p(STA:SA)(5:95), respectively.

Each fatty acid terminated polymer prepared by the above method was melted separately at approximately 85° C. and powdered drug, either marcaine free base or marcaine HCl, was mixed thoroughly into it. The molten mixture was transferred into molds and allowed to solidify. The thus formed drug-polymer compositions were removed from the molds and cut into rectangular slabs weighing approximately 120 mg each. The drug content of each slab was 10% w/w.

Sustained drug release studies for each composition were conducted in 20 ml scintillation vials using 20 ml of 0.1 M phosphate buffer at 37° C. The marcaine released to the releasing medium was determined by HPLC, C18 reverse phase column using 60:40 acetonitrile:0.1 M phosphate buffer at a pH of 6.8 and a flow rate of 1 ml/minute. The amount of marcaine free base and marcaine HCl salt released from the various polymers as a function of time is represented in FIGS. 1 and 2, respectively. It is evident from the figures that increasing the ratio of stearic acid prepolymer to sebacic acid prepolymer in the fatty acid terminated polymers decreases the release rate of the drug from the compositions. The release rate of the drug becomes almost linear at a stearic acid:sebacic ratio of 15:85.

EXAMPLE 3

Release of Bovine Serum Albumin from Fatty Acid Terminated Polyanhydride

Bovine serum albumin ("BSA") (0.1 gm) was uniformly dispersed in molten samples of 40% stearic acid:60% sebacic acid and 50% stearic acid:50% sebacic acid fatty acid terminated polyanhydride (0.8 gm each) which were prepared according to the method of Example 1. The molten dispersion was compressed between two glass plates covered with teflon coated aluminum foil. After cooling, the film was separated from the foil and cut into particles of less than 1 mm in diameter. The in vitro release of BSA from the microparticles was carried out in phosphate buffer (pH 7.4) at 37° C. The concentration of BSA in the releasing medium was determined by HPLC using a size exclusion column (BioRad TSK gel) and 10% acetonitrile in pH 6.8 buffer solution at a flow rate of 1 ml/minute. The drug was detected by UV at 214 nm.

The release profile is as shown in FIG. 3. After an initial burst, the release of BSA was essentially linear for two weeks.

EXAMPLE 4

Release of Spray Dried Somatotropin from Fatty Acid Terminated Polyanhydride

Microparticles of fatty acid terminated polyanhydride containing bovine somatotropin were prepared as described in Example 3, using sebacic acid and stearic acid in a ratio of 85:15. The in vitro release of the somatotropin from the microparticles was determined over time, using the method described in Example 2.

About 60% of the drug was released in an active form from the fatty acid terminated polyanhydride over a period of 96 hours as determined by HPLC analysis. In comparison, only about 30-40% of drug was released in active form from p(SA).

EXAMPLE 5

Preparation of Microparticles of Fatty Acid Terminated Polyanhydride Containing Stabilized rbSt A. Preparation of Stabilized Bovine Somatotropin (rbSt)

Recombinant bovine somatotropin (rbSt) (150 mg) and a stabilizer (37 mg) were dissolved in 200 ml of highly purified water. The solution was then transferred to a lyophilization flask, pre-frozen in a dry ice/acetone bath, and lyophilized by standard methods. The resulting white crystalline powder was then reduced to the desired particle size by triturating it in a mortar with pestle. The stabilizers evaluated were sucrose, potassium carbonate, sodium sulfate, deoxycholic acid and polysorbate 80. In the case of polysorbate 80, the amount of rbSt and stabilizer were 100 mg and 5 mg, respectively.

B. Preparation of rbSt Containing Fatty Acid Terminated Polymers

Microparticles of fatty acid terminated polyanhydride were prepared by combining stabilized rbSt (75 mg) with fatty acid terminated polyanhydride (85:15 SA:STA) (300 mg) to obtain 20% w/w loading. Stabilized rbSt was added to the polymer pre-melted at 82° C. The melt dispersion was mixed thoroughly with a spatula and cast into a thin film. The thin film was then ground into particles of the desired average size by methods well known to those skilled in the art.

Using the method of Example 2, it was determined that almost 100% of the drug was released in an active form over a period of 3 days.

EXAMPLE 6

In vivo Release of Porcine Somatotropin from Fatty Acid Terminated Polyanhydride In Vivo A film of fatty acid terminated polyanhydride (85:15 SA:STA) (0.8 gm), containing porcine somatotropin (0.2 gm) was prepared as described in Example 4. The film was then crushed to obtain microparticles of less than 63μ in diameter. The microparticles were suspended in polyethylene glycol (PEG 200) and the solution was injected subcutaneously into rats. Blood samples were taken at regular time intervals and serum was analyzed for porcine somatotropin by RIA assay.

The release of porcine somatotropin from the microparticles was more prolonged than the release obtained by injecting a solution of porcine somatotropin alone.

The desirable chemical and physical properties of the fatty acid terminated polyanhydrides permit the polymers to be formed into specific structures and used, for example, as laminates for degradable or nondegradable fabrics, as coatings for implantable devices, as barriers for adhesion prevention, as tubes for nerve generation, and in guided tissue regeneration for periodontal disease, as well as for controlled drug delivery. These and other variations of the present invention will become apparent to one skilled in the art. Such other embodiments are intended to fall within the scope of the appended claims.

We claim:

1. A fatty acid terminated polyanhydride.

2. The fatty acid terminated polyanhydride of claim 1 of the formula:

wherein R is an aliphatic, aromatic, or heterocyclic moiety, R' is a linear fatty acid residue of $C_6$ to $C_{22}$, and n is an integer from 1 to 500.

3. The fatty acid terminated polyanhydrides of claim 1 formed by polymerizing fatty acid prepolymers and dicarboxylic acid prepolymers.

4. The fatty acid terminated polyanhydrides of claim 1 wherein the fatty acid is selected from the group consisting of caproic acid, caprylic acid, capric acid, lauric acid, myristic acid, palmitic acid, stearic acid, arachidic acid, behenic acid, lignoceric acid, heptanoic acid, nonanoic acid, undecanoic acid, tridecanoic acid, pentadecanoic acid, heptadecanoic acid, nonadecanoic acid, heneicosanoic acid, tricosanoic acid, arachidonic acid, docosahexanoic acid, elaidic acid, erucic acid, linoleic acid, linolenic acid, nervonic acid, oleic acid, palmitoleic acid and petriselinic acid.

5. The fatty acid terminated polyanhydrides of claim 1 prepared by polymerization or copolymerization of a dicarboxylic acid selected from the group consisting of $HOOC-H_2C-Y-CH_2-COOH$; aromatic dicarboxylic acids, as defined by the formulas:

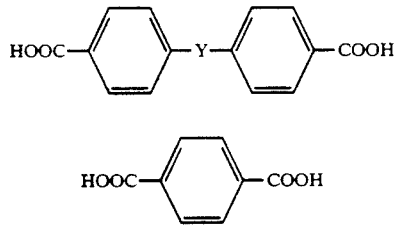

aromatic-aliphatic dicarboxylic acid, as defined by the formula:

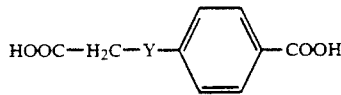

aliphatic heterocyclic dicarboxylic acids defined by the formula:

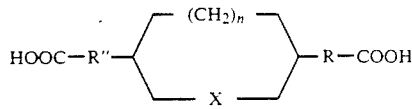

wherein $X=O$, N or S, $n=1$ to 3; $R=R''=$ an aliphatic, aromatic or heteroaromatic moiety, and Y is a divalent organic radical; aromatic heterocyclic dicarboxylic acids, and aliphatic aromatic heterocyclic dicarboxylic acids; with a fatty acid.

6. The fatty acid terminated polyanhydrides of claim 1 prepared by polymerization or copolymerization of a dicarboxylic acid selected from the group consisting of sebacic acid, phthalic acid, terephthalic acid, isophthalic acid, adipic acid, 1,10-dodecanoic acid, bis(p-carboxyphenoxyalkane), fumaric acid, 1,4-diphenylenediacrylic acid, branched monomers such as 1,3,5-benzenetricarboxylic acid, azeleic acid, pimelic acid, suberic acid (octanedioic acid), itaconic acid, biphenyl-4,4'-dicarboxylic acid, and benzophenone-4,4'-dicarboxylic acid, p-carboxyphenoxyalkanoic acid, hydroquinone-0,0-diacetic acid, 1,4-bis-carboxymethyl benzene, 2,2-bis-(4-hydroxyphenyl)propane-0,0-diacetic acid, 1,4-phenylene-dipropionic acid, and cyclohexane dicarboxylic acid or their anhydrides or acid chlorides with a fatty acid.

7. The fatty acid terminated polyanhydrides of claim 1 prepared by the polymerization of sebacic acid and stearic acid, or their anhydrides or acid chlorides.

8. The fatty acid terminated polyanhydride of claim 1 wherein the fatty acid and the dicarboxylic acid, or their anhydrides or acid chlorides, are combined in a ratio of 2 to 1000 fatty acid units per 500 units of dicarboxylic acid monomers 9. The fatty acid terminated polyanhydride of claim 1 wherein the fatty acid and the dicarboxylic acid are mixed in a ratio of approximately 15% fatty acid prepolymer to approximately 85% dicarboxylic acid prepolymer by weight.

10. The fatty acid terminated polyanhydride polymers of claim 1 wherein the polymers are soluble in organic solvents.

11. The fatty acid terminated polyanhydride polymers of claim 1 wherein the polymers are prepared by melt polycondensation.

12. The fatty acid terminated polyanhydride polymers of claim 1 further comprising a substance to be released from the polyanhydride polymers selected from the group of proteins, carbohydrates, and organic molecules.

13. The fatty acid terminated polyanhydride polymer of claim 12 wherein the substance to be released is selected from the group consisting of chemotherapeutic agents, antibiotics, antivirals, antifungals, antiinflammatories, and anticoagulants.

* * * * *